United States Patent [19]

Weiner et al.

[11] Patent Number: 5,338,829
[45] Date of Patent: Aug. 16, 1994

[54] PEPTIDES DERIVED FROM HUMAN IMMUNODEFICIENCY VIRUS-1 GP160

[75] Inventors: David B. Weiner, Penn Wynne; Mark I. Greene, Penn Valley; William V. Williams, Havertown, all of Pa.

[73] Assignee: Trustees of the University of Pennsylvania, Philadelphia, Pa.

[21] Appl. No.: 932,078

[22] Filed: Oct. 19, 1992

Related U.S. Application Data

[63] Continuation of Ser. No. 582,889, Oct. 4, 1990, abandoned, which is a continuation-in-part of Ser. No. 183,840, Apr. 20, 1988, abandoned.

[51] Int. Cl.⁵ .................. A61K 37/02; C07K 3/00; C07K 5/00; C07K 15/00
[52] U.S. Cl. .................. 530/324; 530/325; 530/350
[58] Field of Search .................. 530/324, 325, 350; 435/5

[56] References Cited

U.S. PATENT DOCUMENTS

| | | | |
|---|---|---|---|
| 4,490,358 | 12/1984 | Greene et al. | 424/86 |
| 4,520,113 | 5/1985 | Gallo et al. | 435/5 |
| 4,722,888 | 2/1988 | Broder et al. | 435/5 |
| 4,725,669 | 2/1988 | Essex et al. | 530/322 |
| 4,743,678 | 5/1988 | Essex et al. | 530/350 |

OTHER PUBLICATIONS

Zhou et al., The Journal of Immunology, 139(9):2950–2956 (1987).
Wang et al., Proceeding of the National Academy of Science, U.S.A., 83:6159–6163 (1986).
McDougal et al., The Journal of Immunology, 137(9):2937–2944 (1986).
Sattentau et al., Science, 234:1120–1123 (1985).
Chanh et al., Proceedings of the National Academy of Science, U.S.A., 84:3891–3895 (1987).
Banapour et al., The Journal of Immunology, 139:4027–4033 (1987).
Dalgleish et al., Nature, 312:763–767 (1984).
Sodroski et al., Nature, 322:470–474 (1984).
McCune et al., Cell, 53:55–67 (1988).
Burstin et al., Virology, 117:146–155 (1982).
International Search Report for application Ser. No. PCT/US89/01621.
Chiodi et al., Journal of Medical Virology 23:1–9 (1987).
Gnann et al., Journal Inf. Dis. 156(2):261–267 (1987).
Ho et al., Journal of Virol., 61(6):2024–2028 (1987).

*Primary Examiner*—Christine M. Nucker
*Assistant Examiner*—Lynette F. Smith
*Attorney, Agent, or Firm*—Woodcock Washburn Kurtz Mackiewicz & Norris

[57] ABSTRACT

This invention discloses novel polypeptides having an antigenic determinant or determinants immunologically cross-reactive with determinants of a glycoprotein having a molecular weight of approximately 41,000 daltons, and determinants of a glycoprotein having a molecular weight of approximately 160,000 daltons which are obtained from cells infected with human immunodeficiency virus-1. The invention further discloses novel polypeptides having an antigenic determinant or determinants specific for a glycoprotein having a molecular weight of approximately 41,000 daltons obtained from cells infected with human immunodeficiency virus-1, the polypeptides further having an antigenic determinant or determinants immunologically cross-reactive with at least one glycoprotein having a molecular weight of 25,000 to 35,000 daltons, 45,000 daltons to 60,000 daltons, 80,000 to 100,000 daltons or 180,000 or 220,000 daltons, which are obtained from HSB, St, HeLa and human cells. The novel polypeptides of the invention are useful in methods of interfering with the effects of HIV-1 upon host cells having cell surface polypeptides capable of binding HIV-1. Methods of assay for HIV-1 infection are also disclosed. The invention also discloses peptides having amino acid sequences of about 10 to about 50 amino acids that correspond to at least a portion of an epitope of HIV and methods for developing such biologically active peptides.

5 Claims, 7 Drawing Sheets

PEPTIDES DERIVED FROM HUMAN IMMUNODEFICIENCY VIRUS-1 GP160

This is a continuation of application Ser. No. 582,889, filed Oct. 4, 1990 now abandoned which is a continuation-in-part of Ser. No. 183,840, filed Apr. 20, 1988 now abandoned.

FIELD OF THE INVENTION

The present invention relates to the field of treatments and diagnostics for viral infection. More particularly, this invention relates to the field of treatments and diagnostics for infection by the human immunodeficiency virus-1.

REFERENCE TO RELATED APPLICATIONS

This application is a continuation-in-part application of U.S. patent application Ser. No. 183,840 filed Apr. 20, 1988 in the names of Mark I. Greene, William V. Williams and David Weiner, entitled "Methods of Modulating Retro-Virus Host Cell Interactions", which application is specifically incorporated as if fully set forth herein.

BACKGROUND OF THE INVENTION

Acquired Immune Deficiency Syndrome (AIDS) is one of the most feared diseases in the world today. Infection with the human immunodeficiency virus (HIV-1), believed to be the cause of AIDS is almost always fatal. Symptoms of the disease can take years to develop, thus facilitating the spread of this fatal disease by persons unknowingly harboring the virus. Treatments for AIDS are limited and have been unsuccessful in controlling the disease.

HIV-1 has been shown to preferentially infect cells expressing the CD4, a 55,000 dalton cell surface glycoprotein. This tropism is believed to result from interactions between the virus envelope gp120 and a high affinity binding site on the CD4 glycoprotein which permits viral adsorption- gp120 is part of the envelope glycoprotein gp160. This larger glycoprotein consists of two main glycoprotein portions - gp120 and gp41. gp120 is believed to be the outermost part of the complex made up of these two glycoproteins. gp41, the inner portion of the complex, is embedded in the viral membrane. Following the initial attachment of virus to the cell surface CD4 molecule, gp41 pierces the membranes of the target cell and initiates fusion. This interaction precedes viral entry, uncoating, and replication.

U.S. Pat. No. 4,520,113 issued May 28, 1985 to Gallo et al. discloses methods of detecting HTLV-III (now named HIV-1) in sera of AIDS and pre-AIDS patients. These methods detect the presence of antibodies in the patient's serum which bind to antigenic sites on HIV-1 or fractions of HIV-1, thus signalling the presence of the virus itself in the patient. A fraction known as gp41, a 41,000 dalton viral envelope protein was found to be particularly useful in the diagnostic methods of the invention because many persons having AIDS or pre-AIDS illnesses were found to have antibodies against this viral protein.

U.S. Pat. No. 4,725,669 issued Feb. 16, 1988 to Essex and Lee discloses novel polypeptides along with assays which use the polypeptides to detect infection of cells by human T-cell lymphotrophic virus-III (i.e. HIV-1). The polypeptides may be purified forms of glycoproteins found in the cell surface membrane of cells infected with human T-cell lymphotrophic virus-III. The polypeptides contain antigenic determinants immunologically cross-reactive with glycoproteins having a molecular weight of 120,000 daltons and 160,000 daltons which occur on the surface of cells infected with HTLV-III (HIV-1).

Treatment of individuals infected with HIV-1 has been complicated by the binding capacity of the virus to mammalian cells and the extreme toxicity of infection with the virus. The potential for inadvertently infecting healthy individuals with only partially inactivated whole HIV-1 or components of the virus as part of a vaccine is very high. One commercially available compound which is useful as an anti-infective agent is a form of CD4. The compound is believed to work because it binds the gp120 as tightly as the natural CD4. In this way, if given in high enough concentrations, the free (administered) CD4 will bind all of the viral gp120 and prevent its binding CD4 on host cells. Efforts to control the virus through drugs has not succeeded. Alternate means of treating individuals infected with HIV-1, as well as alternate means of preventing or inhibiting infection of cells with HIV-1 are needed which are not toxic to the individual infected with HIV-1 and are safe for individuals not infected with the virus.

A major problem with retroviral infections is the manner in which the retroviruses are able to subvert the host organism's immune response to the detriment of the host. This is illustrated most vividly by the effect of HIV infection on human helper T cells. HIV-1 infects cells by first binding to host cell CD4 molecules utilizing the viral envelope glycoprotein gp120, and subsequently fusing with the cell membrane. In an infected cell, gp120 is expressed on the surface of the cell, creating a potential target for cytolytic antibody responses. Superficially, an antibody response to gp120 would seem to be advantageous to the host. However, during HIV infection, large amounts of gp120 are also shed from infected cells, with subsequent binding to CD4 molecules on uninfected cells- These uninfected cells also become targets for cytolytic antibody binding and subsequent lysis. Among CD4 bearing cells in the host are helper T cells, the very cells necessary for the development of antibody responses. By shedding gp120 from infected cells, HIV is able to cripple an essential arm of the immune response that would lead to elimination of HIV.

Accordingly, it is an object of the invention to provide agents and methods to inhibit infection of cells by HIV-1. A further object is to provide polypeptides capable of effecting such inhibition. Another object is to interfere with the binding of HIV-1 to host cells. A further object is to provide methods for detecting the presence or HIV-1 In biological specimens or of detecting the presence of antibodies for HIV-1 in such specimens.

It would obviously be beneficial to the host develop antibody responses that are able to recognize and destroy infected cells, while leaving uninfected cells intact. Thus it is also an object of the invention to provide such antibodies. It is a further object of the invention to provide methods for the recognition of sites on retroviruses that are immunogenic and lead to the development of beneficial antibodies of this type. These and other objects will become apparent from a review of the instant specification.

SUMMARY OF THE INVENTION

Figure 1:
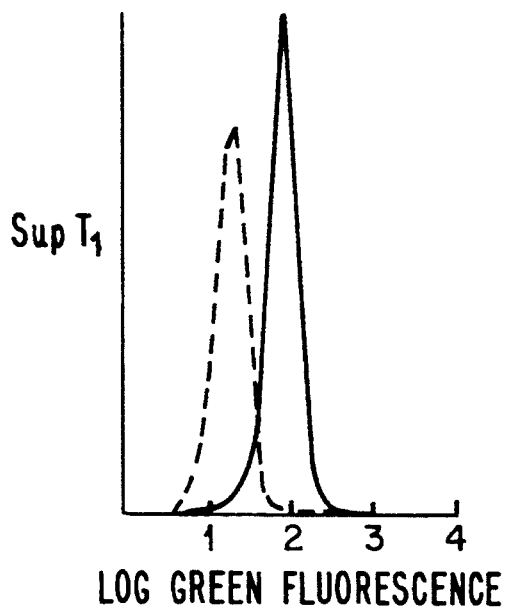
FIGS. 1 through 9 show binding of anti-H156 sera to murine L cells.
Figure 2:
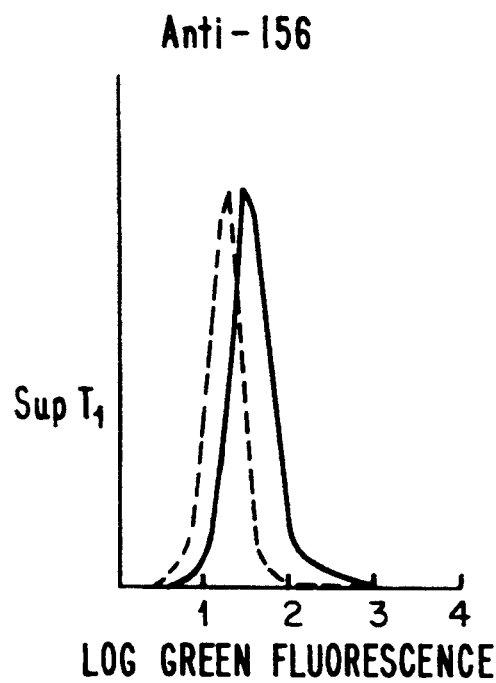
Figure 3:
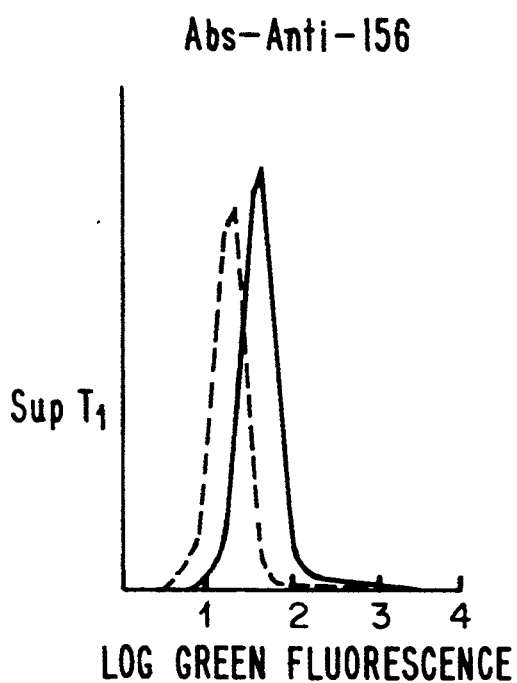
Figure 4:
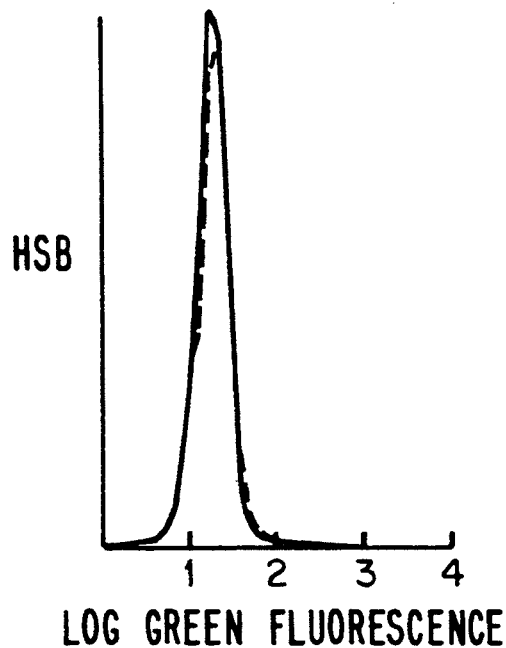
Figure 5:
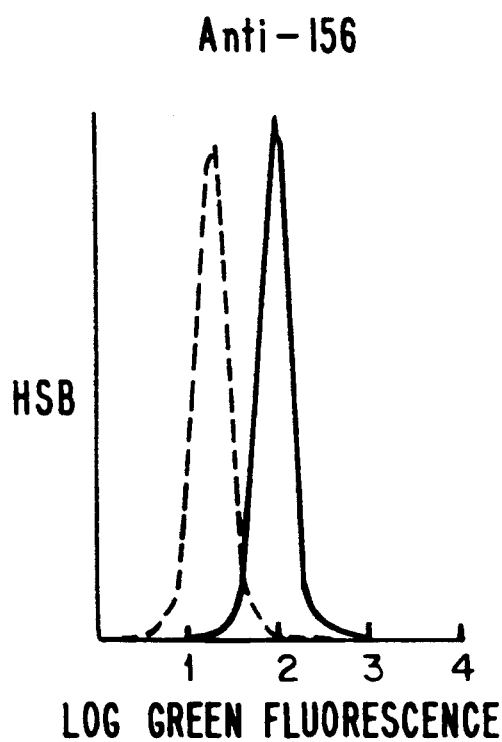
Figure 6:
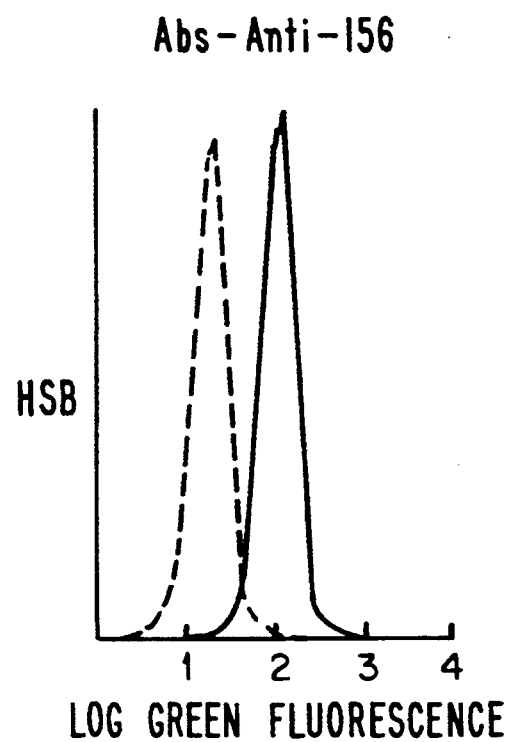
Figure 7:
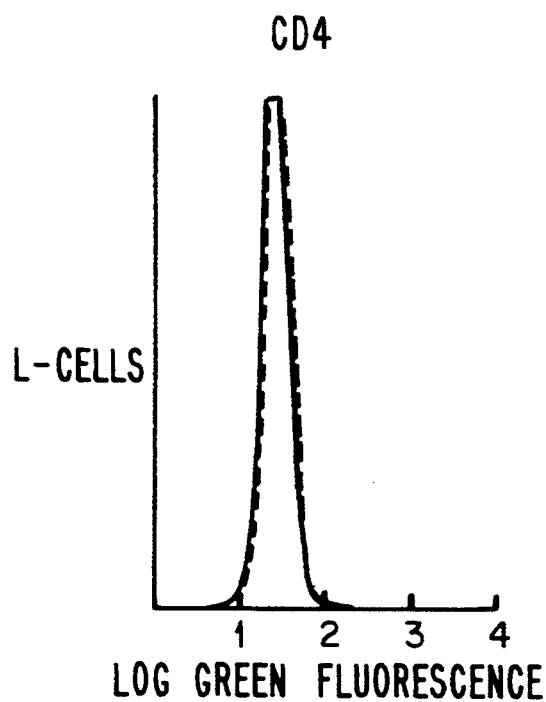
Figure 8:
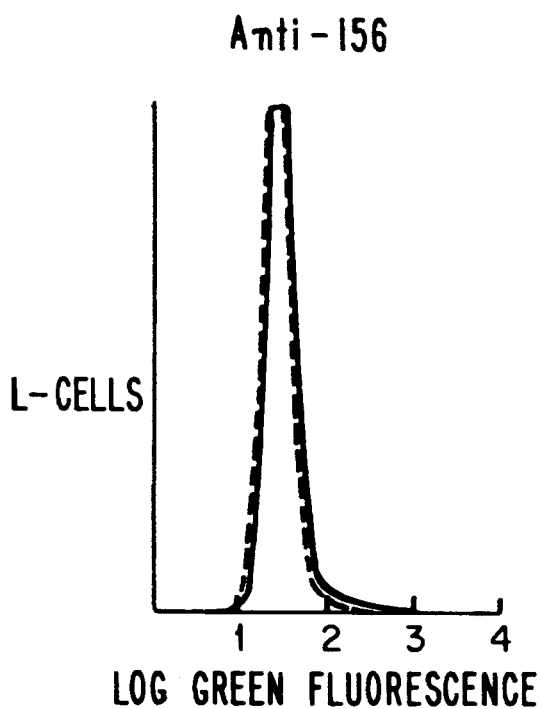
Figure 9:
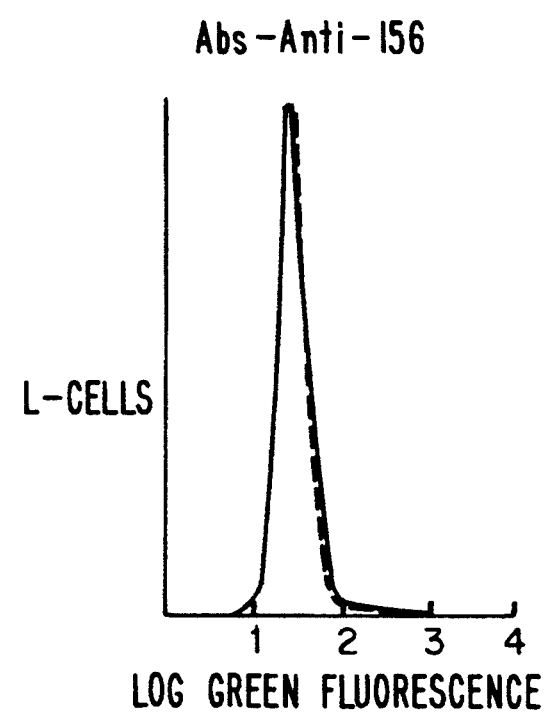

The present invention discloses novel receptors present on cells which bind gp41 which have not heretofore been described. These receptors appear to regulate the entry of HIV-1 into cells subsequent to the binding of the virus to the cell at the CD4 receptor by gp120.

The present invention further discloses novel antibodies which are specific for the antigenic site of gp41 which binds the novel receptors. It is now believed that these antibodies are at least partly responsible for the inhibition of syncytia formation which occurs when human cells are infected with HIV-1. It is believed that gp41 has at least two antigenic determinants and that at least one of them binds to polypeptides on the surface of a host cell. Antibodies specific for the antigenic determinant of gp41 which binds to the novel receptors have the ability to inhibit formation of syncytia, whereas other antibodies to gp41 previously known do not inhibit formation of syncytia. Antibodies to gp41 are known to occur in person infected with HIV-1, however these antibodies are now believed to be specific for an antigenic determinant or determinants not associated with binding of HIV-1 to the host cell.

The discovery of a second binding site which appears to regulate the entry of HIV-1 into cells and novel antibodies specific for gp41 at the antigenic determinant which binds to the second receptor provides a substantial advance in treatment of cells by inhibiting infection. The discovery of a second binding site and novel antibodies to gp41 also provide methods and agents for inhibiting infection of cells. This second binding site is believed to be comprised of one or more glycoproteins having molecular weights of 25,000 to 35,000 daltons, 45,000 daltons to 60,000 daltons, 80,000 to 100,000 daltons and 180,000 to 220,000 daltons. The second binding site binds gp41 an envelope glycoprotein of HIV-1.

The present invention provides novel agents for interfering with the effects of HIV-1 upon host cells having surface polypeptides capable of binding HIV-1. The invention provides substantially pure polypeptides having an antigenic determinant or determinants immunologically cross-reactive with of a glycoprotein having a molecular weight of approximately 41,000 daltons, and determinants of a glycoprotein having a molecular weight of approximately 160,000 daltons; each of the glycoproteins being obtained from cells infected with human immunodeficiency virus - 1. Polypeptides suitable for use in the invention include anti-idiotype antibodies having the appropriate antigenic determinants. The glycoprotein known as gp41 which has a molecular weight of 41,000 daltons and is obtained from cells infected with HIV-1 contains a polypeptide region which has an appropriate antigenic determinant and is suitable for use in the invention.

By "polypeptides containing immunologically cross-reactive antigenic determinants" is meant polypeptides having in common antigenic determinants with which a given antibody will react.

The invention also provides novel polypeptides comprising substantially pure polypeptides having an antigenic determinant or determinants specific for a glycoprotein having a molecular weight of approximately 41,000 daltons which obtained from cells infected with human immunodeficiency virus-1, the polypeptides further having an antigenic determinant or determinants immunologically cross-reactive with at least one glycoprotein having a molecular weight of 25,000 to 35,000 daltons, 45,000 daltons to 60,000 daltons, 80,000 to 100,000 daltons or 180,000 to 220,000 daltons. The glycoproteins are preferably obtained from HSB, ST, HeLa and human cells. The polypeptides are also useful in methods of interfering with the effects of HIV-1 upon host cells having surface polypeptides capable of binding HIV-1. Antibodies and glycoproteins are examples of polypeptides which may provide a suitable antigenic determinant or determinants for use in the invention.

The invention further provides methods of interfering with the effects of human immunodeficiency virus - 1 upon host cells having cell surface polypeptides capable of binding human immunodeficiency virus - 1. These comprise polypeptide having an antigenic determinant or determinants immunologically cross-reactive with determinants of a glycoprotein having a molecular weight of approximately 41,000 daltons, and determinants of a glycoprotein having a molecular weight of approximately 160,000 daltons, each of which glycoproteins are obtained from cells infected with human immunodeficiency virus - 1 is contacted with the cells under conditions selected to permit the polypeptide to bind to the host cell surface polypeptides thereby inhibiting the virus from binding to the cell surface polypeptide to effect the interference.

In accordance with other embodiments of the invention, methods of interfering with the effect of human immunodeficiency virus-1 upon host cells having cell surface polypeptides capable of binding human immunodeficiency virus - 1 are provided. These comprise contacting human immunodeficiency virus -1 with a polypeptide having an antigenic determinant or determinants specific for a glycoprotein having a molecular weight of approximately 41,000 daltons, which is obtained from cells infected with human immunodeficiency virus - 1; the polypeptide further having an antigenic determinant or determinants immunologically cross-reactive with at least one glycoprotein having a molecular weight of 25,000 to 35,000 daltons, 45,000 daltons to 60,000 daltons, 80,000 to 100,000 daltons or 180,000 to 220,000 daltons. These glycoproteins are obtained from HSB, ST, HeLa and human cells. The contacting is effected under conditions selected to permit the polypeptide to bind to the virus thereby inhibiting binding of the virus to the host cells and affecting the interference.

Methods for detecting the presence of neutralizing antibodies to HIV-1 in biological specimens suspected of containing HIV-1 are also provided. The biological specimen is contacted with a polypeptide having an antigenic determinant or determinants immunologically cross-reactive with determinant of a glycoprotein having a molecular weight of approximately 41,000 daltons, and determinants of a glycoprotein having a molecular weight of approximately 160,000 daltons, each of the glycoproteins being obtained from cells infected with human immunodeficiency virus - 1, under conditions selected to permit binding of the polypeptide to neutralizing antibodies in the biological specimen. The polypeptide is then detected. In preferred embodiments of the invention the polypeptide is detectably labeled with a label known in the art. Using these methods the course of treatment of cells with neutralizing antibodies or polypeptides can be followed.

The invention additionally provides further methods of detecting the presence of human immunodeficiency virus - 1 in biological specimens suspected of containing the virus. These methods comprise contacting the biological specimen with a polypeptide having an antigenic determinant or determinants specific for a glycoprotein having a molecular weight of approximately 41,000 daltons, which is obtained from cells infected with human immunodeficiency virus - 1; the polypeptide further having an antigenic determinant or determinants immunologically cross-reactive with at least one glycoprotein having a molecular weight of 25,000 to 35,000 daltons, 45,000 daltons to 60,000 daltons, 80,000 to 100,000 daltons or 180,000 to 220,000 daltons, these glycoproteins being obtained from HSB, ST, HeLa and human cells, under conditions selected to permit binding of the polypeptide to the virus in the biological specimen. The peptide is then detected, in preferred embodiments of the invention, the peptide is detectably labeled with a label known in the art.

The invention further provides methods of determining the presence of neutralizing antibodies to human immunodeficiency virus-1 in serum of humans which antibodies inhibit formation of syncytia. Human serum is contacted with a mixture of cells capable of forming syncytia in the presence HIV-1 and cells infected with HIV-1 with human serum under conditions selected to allow binding of neutralizing antibodies to said cells. The formation of syncytia are then detected. In preferred embodiments of the invention, the neutralizing antibodies have an antigenic determinant or determinants specific for a glycoprotein having a molecular weight of approximately 41,000 daltons which is obtained from cells infected with human immunodeficiency virus - 1; the polypeptide further having an antigenic determinant or determinants immunologically cross-reactive with at least one glycoprotein having a molecular weight of 25,000 to 35,000 daltons, 45,000 daltons to 60,000 daltons, 80,000 to 100,000 daltons or 180,000 to 220,000 daltons, these glycoproteins being obtained from HSB, ST, HeLa and human cells.

The invention also provides methods of treating cells having cell surface polypeptides capable of binding human immunodeficiency virus -1 to inhibit infection by HIV-1. Agents which block the gp41 binding site on the cells are provided and these agents are administered to the cells under conditions selected to allow binding of the agents to the cells thereby blocking the gp41 binding site and inhibiting infection of the cells. In preferred embodiments of the invention, agents which block the gp41 binding site on the cells are those polypeptides which have an antigenic determinant or determinant immunologically cross-reactive with determinants of glycoprotein having a molecular weight of approximately 41,000 daltons, and determinants of a glycoprotein having a molecular weight of approximately 160,000 daltons; each of the glycoproteins being obtained from cells infected with HIV-1.

The invention additionally provides methods of inhibiting HIV-1 infection of cells having cell surface polypeptides capable of binding gp41 on HIV-1. Agents which bind to gp41 are provided and these agents are administered to HIV-1 under conditions selected to allow binding of the agent to gp41, thereby blocking gp41 and making it unavailable for binding to cells and thus inhibiting infection of the cells. In preferred embodiments of the invention, the agents which bind to gp41 are polypeptides having an antigenic determinant or determinants specific for a glycoprotein having a molecular weight of approximately 41,000 daltons, this glycoprotein being obtained from cells infected with human immunodeficiency virus - 1; the polypeptide further having an antigenic determinant or determinants immunologically cross-reactive with at least one glycoprotein having a molecular weight of 25,000 to 35,000 daltons, 45,000 daltons to 60,000 daltons, 80,000 to 100,000 daltons or 180,000 to 220,000 daltons, these glycoproteins being obtained from HSB, ST, HeLa and human cells.

The invention further provides peptides having an amino acid sequence of about 10 to about 50 amino acids that corresponds to at least a portion of an epitope of HIV. These peptides correspond to regions of the HIV envelope glycoprotein gp160 that "protect" or inhibit infection and syncytia formation of human lymphocytes or other susceptible cell, when peptides corresponding to at least a portion of the region are contacted with cells having receptors for HIV-1. without wishing to be bound by any theory or mode of action, it is believed that the peptides correspond to regions of gp160 (or gp120 and gp41) that are involved with binding of HIV to receptors on the surface of human cells. The peptides of the invention may bind to these receptors, thus making the receptors unavailable for binding HIV. The peptides of the invention may also be used to elicit antibodies to prevent virus from binding to receptors on the surface of human cells. The peptides of the invention are preferably selected from the group consisting of gly-glu-ile-lys-asn-cys-ser-phe-asn-ile-ser-thr-ser-ile-arg-gly-lys-val-gln-lys-glu-tyr-ala;
asn-gly-asn-ala-glu-glu-val-val-ile-arg-ser-ala-asn-phe-thr-asp-asn-ala-lys-thr-ile-ile-val;
cys-asn-ile-ser-arg-ala-lys-trp-asn-asn-thr-leu-lys-gln-ile-asp-ser-lys-leu-arg-glu-gln-phe;
gly-ser-asp-thr-ile-thr-leu-pro-cys-arg-ile-lys-gln-ile-ile-asn-met-trp-gln-glu-val-gly-lys; val-gln-gln-gln-asn-asn-leu-leu-arg-ala-thr-glu-ala-gln-gln-his-leu-leu-gln-leu-thr-val-trp- gly-ile-lys-gln-leu-gln; and
peptides containing these sequences.

The invention also provides antibodies specific for a peptide of the invention described above.

The invention provides methods of developing or synthesizing biologically active peptides. The binding patterns of antibodies from a healthy individual infected with a retrovirus and antibodies from a symptomatic individual infected with the retrovirus are compared to determine at least one binding region unique to antibodies from healthy, infected individual. A peptide corresponding to at least a portion of a unique binding region is then synthesized.

The comparing step preferably comprises the steps of providing at least one test peptide derived from the amino acid sequence of a component of said retrovirus; contacting antibodies from a healthy, infected individual and a symptomatic, infected individual with at least one test peptide to determine the presence of antibodies bindable with the test peptide; comparing the results of the second step for the healthy, infected individual and the symptomatic, infected individual to determine at least one binding region unique to antibodies from the healthy, infected individual.

Mouse cells do not have the CD 4 receptor on their surface and cannot be infected with the AIDS virus under normal conditions. Mouse cells in which DNA encoding for CD 4 has been inserted into the expressed genetic material, however, can be shown to express CD 4 on their surfaces and are capable binding the AIDS virus. They are not, however, infected by virus. Human cells which do not express CD 4 are also generally not infectable by the virus, but if they are made to have CD 4 on their surfaces they can be infected, indicating that CD 4 alone is insufficient to produce infectability, and that there is some other element expressed on human cell surfaces required for actual infectability.

Mouse antibodies which are similar in structure to the functional part of the GP 41 act as probes to cell surface proteins which function as a GP 41 receptor. Cells that have CD 4, but do not bind the GP 41 look-alike are not infectable with the AIDS virus. Once cells are infected with AIDS virus, they begin to manifest the glycoproteins encoded for by the AIDS virus on their own surfaces. Because these cells have the proteins which lead to fusion of the AIDS virus membrane with the human cell membrane, they tend to fuse together themselves through the same molecular mechanisms involved in infection forming what are called syncytia. Both the mouse antibodies, and the human antibodies from which they are derived are capable blocking the formation of syncytia between infected cells, indicating that either binding of the GP 41 active site, binding of the human receptor site is capable of preventing fusion. This is believed to mean that either is capable preventing cellular infection, since fusion is an essential step to such infection.

Serum from patients with high levels of antibodies GP 120 does not prevent the fusion of such cellular membranes and is further evidence that antibodies to GP 120 are protective against infection.

It is known that persons infected with HIV-1 produce antibodies to gp41; however, not all of these antibodies have a neutralizing or inhibiting effect upon the ability of HIV-1 to enter susceptible cells. Those antibodies which have a neutralizing effect are within the scope of the invention. It is believed that gp41 has at least two antigenic determinants and that at least one of them binds to polypeptides on the surface of a host cell. Non-neutralizing antibodies are believed to be specific for an antigenic determinant or determinants not principally associated with binding of HIV-1 to the host cell, whereas neutralizing antibodies are believed to be directed towards an antigenic determinant or determinants involved with binding of HIV-1 to the host cell. It is these latter antibodies which are especially useful the practice of this invention.

These neutralizing antibodies, which are a source of some of the polypeptides useful in the invention, can be obtained for example by testing the serum of persons with AIDS, ARC or who may have been infected with the virus through contacts with persons infected with the virus. Serum from these persons is tested in the Fusion Inhibition or Syncytia Assay set forth herein or by other methods which determine fusion inhibition. Antibodies which inhibit syncytia formation are selected and used in the invention as sources of sequences of polypeptides having an antigenic determinant or determinants specific for a glycoprotein having a molecular weight of approximately 41,000 daltons which are obtained from cells infected with human immunodeficiency virus - 1, and which further have an antigenic determinant or determinants immunologically cross-reactive with at least one glycoprotein having a molecular weight of 25,000 to 35,000 daltons, 45,000 daltons to 60,000 daltons, 80,000 to 100,000 daltons or 180,000 to 220,000 daltons, said glycoproteins being obtained from HSB, ST, HeLa and human cells.

In accordance with this invention, these antibodies may also serve as a source of antigens for use in making anti-idiotype antibodies. Anti-idiotype antibodies are in effect antibodies to an antibody. The active site of an anti-idiotype antibody contains a functional equivalent of the antigen region for which the antibody is specific. These antibodies can be a source of polypeptides having an antigenic determinant or determinants immunologically cross-reactive with determinants of a glycoprotein having a molecular weight of approximately 41,000 daltons, and determinants of a glycoprotein having a molecular weight of approximately 160,000 daltons, both glycoproteins being obtained from cells infected with human immunodeficiency virus - 1.

Those of ordinary skill in the art will recognize that various modifications can be made in the compounds (polypeptides) of the present invention without departing from the scope hereof. It is contemplated that molecular modelling techniques will permit compounds of different primary and secondary structures to be substituted for the polypeptides of this invention, provided equivalent tertiary structures can be determined. All such modifications may be within certain embodiments of the invention.

Other polypeptides which may be suitable for use in the invention include the unglycosylated moieties of glycoproteins. Other useful polypeptides or proteins, which have the necessary immunogenic determinants, include synthetic polypeptides. Polypeptide fragments of antibodies and anti-idiotype antibodies may also be suitable for use in the invention as may polypeptides produced from recombinant DNA techniques. For example, genes encoding a polypeptide which binds to gp41 or the second receptor can likely be cloned into an expression vector or plasmid which could then be made to produce the polypeptide. Cell lines containing the expression vector which encodes genes for the polypeptide then would provide a source of the polypeptide.

Some of the polypeptides useful in the invention can be purified by electrophoresis of cell lysates or extracts containing the polypeptides with subsequent removal of the polypeptides from the electrophoresis gel to give substantially pure polypeptides. Gel electrophoresis and removal of the polypeptides from gels are readily accomplished using methods known in the art. Other forms of purification may be employed either in addition to or in lieu of the foregoing without deviating from the spirit of the invention. Polypeptides which are immunologically cross-reactive with a glycoprotein having a molecular weight of approximately 41,000 daltons (gp41) which is obtained from cells infected with human immunodeficiency virus - 1 are useful as diagnostic agents to measure levels of anti-gp41 antibodies in biological systems and patients' sera. gp41 is believed to be a viral envelope protein. Antibodies to gp41 have been found in the sera of many AIDS and ARC patients; the presence of antibodies to gp41 is believed to be a reliable indicator of the presence of the virus in cells.

Polypeptides which are immunologically cross-reactive with a glycoprotein having a molecular weight of approximately 41,000 daltons (gp41) which is obtained from cells infected with human immunodeficiency virus -1 are also useful as agents to detect the presence of polypeptide receptors on host cells which are specific for a polypeptide having an antigenic determinant or determinants specific for a glycoprotein having a molecular weight of approximately 41,000 daltons which is obtained from cells infected with human immunodeficiency virus -1, and which polypeptides further have an antigenic determinant or determinants immunologically cross-reactive with at least one glycoprotein having a molecular weight of 25,000 to 35,000 daltons, 45,000 daltons to 60,000 daltons, 80,000 to 100,000 daltons or 180,000 to 220,000 daltons. It is believed that the presence on the surface of cells of polypeptides having the above characteristics determines the capability of cells to become infected with HIV-1. Cells which have CD4 receptors to bind gp120 but which do not have polypeptide receptors as described above do not become infected with HIV-1. Thus the presence of the above polypeptides is a marker for cells that can become infected with HIV-1. Polypeptides which are immunologically cross-reactive with a glycoprotein having a molecular weight of approximately 41,000 daltons (gp41) which is obtained from cells infected with human immunodeficiency virus -1 can be used in methods desired to determine the infectability of cells with HIV-1. These polypeptides are contacted with test cells under conditions selected to permit binding of the polypeptides to the test cells. The polypeptides which have bound to be test cells are then detected. The polypeptides may be detectably labeled using any of the methods known in the art, such as enzymes, for later detection with chromogenic substrates, radiolabels, enzyme-linked immunosorbent assays and the like. Methods of detecting infectability of cells may also combine the use of antibodies to CD4 or other molecules which are capable of binding CD4 to determine the exact infectability status of the cell.

Conventional assay procedures for detecting labeled antigens, antibodies and the like are suitable for use in the methods of the invention which detect the presence of HIV-1 in biological specimens. In preferred embodiments of the invention, for example, the polypeptides may be labeled a radiolabel such as $^{125}I$ or $^{35}S$ for use in radioimmunoassay, with fluorescein for fluorescent immunoassay, with an enzyme for enzyme immunoassay or with biotin for biotin-avidin linked assays. Immobilization assays wherein the polypeptide is bound to an insoluble phase and detection of the virus or antibodies is carried out by measuring their binding to the insoluble phase are also suitable for use in the invention. These methods are exemplar only and other methods may be useful in the invention.

Biological specimens such as blood, serum, lymphocytes, urine, tissues, saliva, feces, and the like may be tested using the methods of the invention. The particular method employed to prepare a specimen for use in the methods of the invention will vary according to the type of specimen and preparation may be easily accomplished using methods known in the art. Screening of blood-derived products, such as vaccines, can also be done by the methods of the invention.

Polypeptides which are immunologically cross-reactive with a glycoprotein having a molecular weight of approximately 41,000 daltons (gp41) which is obtained from cells infected with human immunodeficiency virus -1 may also be used as antigenic substances for the production of antibodies.

Polypeptides having an antigenic determinant or determinants specific for a glycoprotein having a molecular weight of approximately 41,000 daltons which is obtained from cells infected with human immunodeficiency virus -1 and which further have an antigenic determinant or determinants immunologically cross-reactive with at least one glycoprotein having a molecular weight of 25,000 to 35,000 daltons, 45,000 daltons to 60,000 daltons, 80,000 to 100,000 daltons or 180,000 to 220,000 daltons which are obtained from MSB, ST, HeLa and human cells are useful agents for interfering with the infection of cells by HIV-1. These polypeptides are contacted with HIV-1 under conditions selected to allow binding of the polypeptides to the virus and thereby interfere with binding of the virus to host cells. It is believed that these polypeptides would bind to polypeptides which are immunologically cross-reactive with a glycoprotein having a molecular weight of approximately 41,000 daltons (gp41) which is obtained from cells infected with human immunodeficiency virus -1, notably gp41 on the surface of HIV-1. In this way a substantial number of sites by which the virus binds to host cells would already be occupied by the polypeptides of the invention and thus be unavailable for binding to the host. This would result in the virus being unable or severely handicapped in binding to host cells and consequently reduce the rate of infection of cells by the virus.

A wide range of retroviral agents infect mammalian hosts, including HIV-1 & 2, HTLV-1-4, SIV, FeLV, Bovine leukemia virus, and many others. These viruses share a common structural feature in the organization of their membrane glycoproteins. These envelope glycoproteins are synthesized as a single unit, and then cleaved into an external glycoprotein (e.g. gp120) and an integral membrane protein (e.g. gp41) which acts as an anchor for the external glycoprotein. The interaction of these envelope glycoproteins with cellular elements determines the tissue and species tropism of these retroviruses. The immunodominant nature of the external glycoprotein, along with its ability to be shed, is likely to play an important role in the pathogenesis of retroviral infections. The development of substances that bind to the integral membrane protein, without interacting with the external glycoprotein, therefore has utility in targeting vitally infected cells and eliminating them without adverse effects on "innocent bystander" cells. Accordingly, this outlines a general method whereby antibody responses from infected, healthy individuals are utilized to develop substances that bind to the integral membrane protein on infected cells, without binding to uninfected cells, even if they bear the external glycoprotein in their surface.

Thus, antibodies raised to the peptide F560 derived from the sequence of gp41 the integral membrane protein of HIV-1, and preferentially recognized by a healthy infected individual's antibodies, binds to gp-41 bearing cells and targets them for complement mediated lysis. In contrast, antibodies to the peptide F160, derived from the sequence of gp120 the external glycoprotein of HIV-1, bind to gp120 bearing cells and target them for complement mediated lysis regardless of the nature of the association of gp120 with the cell surface (i.e. either expressed endogenously, or adsorbed to the surface of the cells). This strategy is expected to have general utility in developing substances that are capable of binding specifically to retrovirally infected cells without interacting with uninfected cells that bear viral components or receptors.

For other retroviruses, the antibody responses from infected individuals who are healthy or otherwise do not exhibit symptoms of disease associated with infection can be compared with the immune response of infected symptomatic individuals who exhibit symptoms of disease associated with infection to determine epitopes that are unique to the infected healthy individual and not shared by the infected symptomatic individual. Peptides corresponding to at least a portion of the unique protective epitope are synthesized. The peptides can then be used, for production of antibodies or in diagnostic assays.

Comparison of the immune responses can be done as described herein or by other appropriate methods. Test peptides having a length of from about 10 to about 50 amino acids corresponding to portions of retroviral envelope glycoproteins are synthesized or purified from natural sources. Test peptides are selected by arbitrarily dividing the amino acid sequence of the envelope glycoprotein into portions and synthesizing corresponding peptides. Alternatively, test peptides corresponding to exposed portions of the molecule or other regions of interest can be synthesized. Where the amino acid sequence of the glycoprotein has not been determined, peptides can be generated by limited digestion of the molecule that has been isolated from natural sources. The amino acid sequence of peptides can be determined subsequently by conventional techniques for amino acid sequencing.

The test peptides are used to screen serum from healthy, infected individuals and symptomatic, infected individuals in binding assays to determine the presence of antibodies in the sera that bind to the peptides. The results of binding assays constitute the binding profile of the serum. The binding profiles of the sera from the healthy infected individual and the symptomatic infected individual are compared. It may be preferable in some circumstances to use the pooled serum from a number of symptomatic infected individuals in the comparison with the healthy infected individual so that individual variation of immune response is averaged an a representative immune response is used for the comparison. Reactivities in both sera to the same peptide are disregarded. Unique reactivities found in serum from the healthy infected individual thus correspond to important regions of the retroviral envelope, Peptides corresponding to the unique reactivities may then be further tested to determine their usefulness in inhibiting viral replication and for producing antibodies that are capable of binding specifically to retrovirally infected cells without interacting with uninfected cells that bear vital components or receptors.

The peptides of the invention have been derived from epitopes of gp160 the 160,000 dalton envelope glycoprotein of HIV-1. Regions of gp160 have been found contain amino acid sequences which "protect" susceptible cells from infection with the virus or inhibit syncytia formation with infected cells, when peptides corresponding to at least a portion of the region are contacted with susceptible cells. These peptides are set forth in Table 1.

TABLE 1

| Approximate Linear Position On gp160 | Amino Acid Sequence |
|---|---|
| 155–175 (F160) | gly-glu-ile-lys-asn-cys-ser-phe-asn-ile-ser-thr-ser-ile-arg-gly-lys-val-gln-lys-glu-tyr-ala |
| 265–284 | asn-gly-asn-ala-glu-glu-val-val-ile-arg-ser-ala-asn-phe-thr-asp-asn-ala-lys-thr-ile-ile-val |
| 333–351 | cys-asn-ile-ser-arg-ala-lys-trp-asn-asn-thr-leu-lys-gln-ile-asp-ser-lys-leu-arg-glu-gln-phe |
| 415–430 | gly-ser-asp-thr-ile-thr-leu-pro-cys-arg-ile-lys-gln-ile-ile-asn-met-trp-gln-glu-val-gly-lys |
| 552–575 (F560) | val-gln-gln-gln-asn-asn-leu-leu-arg-ala-thr-glu-ala-gln-gln-his-leu-leu-gln-leu-thr-val-trp-gly-ile-lys-gln-leu-gln |

Preferred peptides have an amino acid sequence of about 10 to about 50 amino acids that correspond to at least a portion of a protective epitope of HIV and inhibit syncytia formation of human lymphocyte cells. Other portions of the gp160 molecule that also provide "protection" are also within the scope of the invention. It will be appreciated that modifications of these peptides that retain the protective function are also within the scope of the invention. Such modifications include peptides having an amino acid sequence extending beyond the region of the synthesized peptides in either direction; peptides containing amino acid sequences corresponding to at a least portion of two or more protective regions; peptides having one or more amino acids substituted with other amino acids or other compounds but which still retain the protective function: peptides having a cytotoxic or other molecule attached; or any combination of these. Additionally, the peptides may form part of a larger molecule, such as an antibody or fragment of an antibody. Further it is contemplated that molecular modelling techniques will permit compounds of different primary and secondary structures to be substituted for the polypeptides of this invention, provided equivalent tertiary structures can be determined. All such modifications may be within certain embodiments of the invention.

The peptides of the invention are selected by comparing binding patterns of antibodies from a healthy, infected individual and antibodies from a symptomatic, infected individual to determine at least one binding region unique antibodies from the healthy, infected individual. These unique regions define protective regions or epitopes. Once the protective regions or epitopes have been determined, peptides corresponding to at least a portion of at least one of these regions is prepared. The peptides may be prepared by any convenient methods such as synthesis with the appropriate amine acids and a peptide synthesizer, or by recombinant DNA techniques, where a DNA sequence coding for the amine acid sequence is synthesized or prepared from cellular sources and inserted into an appropriate host cell for production of the peptide. The test peptides may also be prepared by chemical synthesis, recombinant DNA techniques or by purification from natural sources.

For some embodiments of the invention it may be preferable to conjugate the "protective" peptides to a carrier protein such as keyhole limpet hemocyanin. Peptides can be conjugated to carrier proteins by conventional techniques for conjugating proteins. A preferred method for conjugating the peptides and carrier protein is the method described herein. For this method a cysteine residue is added to the amino terminal end of the peptide before conjugation with the carrier protein. This can be conveniently accomplished by chemical synthesis when the peptide is being made or at a later time.

The peptides of the invention are useful as diagnostic reagents. The presence of the protective epitopes in antibodies of persons infected with HIV is a measure of the likelihood of that person developing symptoms of viral infection and progressing to Acquired Immunodeficiency Disease (AIDS) at a later date; the presence of protective antibodies indicating a decreased likelihood of that individual developing symptoms of AIDS. The peptide diagnostic reagents can be used in conventional immunoassays for detecting antigens or antibodies and the presence of protective antibodies in the test sample may be determined by any suitable method, including radiolabel such as $^{125}I$ or $_3{}^5S$ for use in radioimmunoassay with fluorescein for fluorescent immunoassay, with an enzyme for enzyme immunoassay or with biotin for biotin-avidin linked assays. These methods are exemplary only and other methods may be useful in the invention.

For example, the peptides of the invention can be bound to a solid phase such as a multi-well plate. Test samples suspected of containing protective antibodies for HIV are contacted with the peptides under conditions that allow binding of protective antibodies in the test sample to the peptides. Bound protective antibodies are then contacted with an antibody such as anti-human IgG labeled with $^{125}I$ under conditions that allow binding of the labeled antibody to bound protective antibodies. The label is then detected by autoradiographical means. The presence of radiolabel indicates the presence of protective antibodies in the test sample.

The antibodies of the invention can be made by conventional methods for the production of polyclonal or monoclonal antibodies. Polyclonal antibodies can be produced by methods such as the method described herein for producing rabbit antibodies. For monoclonal antibodies, an animal such as a mouse is first injected with the antigen, its spleen cells are removed and fused with myeloma cells to form hybridoma cells, the latter are cloned in a serum-containing medium and the monoclonal antibodies are separated from the medium.

Experimental

Fusion Inhibition Assay

Sup - T1 cells are favored as target cells for their rapid degree of cell fusion when co-cultured with HIV - 1 producing cell lines. Cell culture is performed according to the method of Dalgleish et al, Nature 312: 763, (1984). Sup-T1 cells are plated in 96 well plates ($10^5$ cells/well in RPMI 1640+10% FCS) and incubated with or without dilutions of patient sera mouse sera, or control monoclonal antibodies for 30 minutes at 37 C. HTLV-III B (HIV-1) infected H9 cells are then added $5 \times 10^4$/well and the number of multinucleated giant cells per 16 X field counted with a Zeiss inverted field phase contrast microscope after 18 hours. Syncytia are easily identified and inhibition of syncytia by patient sera or anti-idiotypic antisera can be compared with anti CD4 monoclonal antibody induced syncytia inhibition.

For screening of patient sofa, samples were collected and directly added to syncytia assays and described above at various dilutions. In later assays the HTLV-IIIb (HIV-1) infected H9 cells were replaced with a noninfectious CHO-HIV-1 envelope expressing constructed cell line with fusion capabilities similar to infectious virus, according to the method of Sodroski et al., Nature 322: 470, (1986). At high concentrations, inhibition of syncytia was observed. In contrast, no inhibition of syncytia formation at any concentration was observed when anti-idiotypic antisera generated against pooled AIDS immunoglobulin were used.

Antibodies from one patient, H156, were found to significantly inhibit syncytia formation. These antibodies were used in subsequent experiments and were used to generate anti-idiotype antibodies. References herein to H156 refer to the antibodies from this patient which were obtained through the described screening process.

| | Syncytia Inhibiting Activity | | | | | |
|---|---|---|---|---|---|---|
| | ⅛ | 1/16 | 1/32 | 1/64 | 1/128 | 1/256 |
| Protein A purified | 0 | 0 | 0 | 0 | 0 | 1S |
| IgM fraction | 0 | 0 | 2M | 1M | 2M | 2M |
| H156 sera | 0 | 0 | 0 | 0 | 1M | 2M |
| Normal human sera | 4L | 4L | 4L | 4L | 4L | 4L |

Degree of syncytia formation
4 = Full
0 = None
Size of syncytia formed
S = Small
M = Medium
L = Large

HPLC

Patient sera was extensively dialyzed against phosphate buffer and subjected to gel filtration on high-performance liquid chromatography columns TOYOSDA TSK G 4000–3000 set in series. Samples were analyzed in 10 mM sodium phosphate buffer (PH 7.2). Fractions were run at 0.5 ml/min for 120 min total run. The column was calibrated utilizing molecular weight standards (Sigma). 1 ml fractions were analyzed by syncytia inhibition assays: immunoglobulin fractions were visualized by SDS-PAGE followed by Commassie blue staining. Purified IgG and IgM fractions were stored at −70° until use. Active fractions were observed in two approximate molecular weight ranges of 170 kd and greater than 570 kd. When combined with data from the syncytia inhibiting assay above, this size fractionation suggested syncytia inhibiting activity segregated in the IgG and IgM molecular weight ranges. SDS-polyacrylamide gel electrophoresis of tested fractions revealed the presence of characteristic immunoglobulin bands IgM at molecular weights greater than 590 Kd and IgG in 170Kd fractions supporting this interpretation. Most inactivity was found in the IgG fraction.

Affinity Chromatography

To further demonstrate that antisyncytia activity was mediated by IgG, immunoglobulin fractions were purified by affinity chromatography on protein A agarose beads (Sigma). The protein A-purified antibody mediated significant antisyncytia activity, whereas non protein A binding materials had little activity.

Generation of Anti-idiotypic Antisera 8 to 10 week old female Balb/c mice were inoculated subcutaneously with 100 ugs of protein A-purified H156 IgG or pooled AIDs patient IgG emulsified in complete Freunds adjuvant. following the primary immunization mice were boosted bimonthly with 100 ug antibody emulsified in incomplete Freunds adjuvant. One week following the fourth and subsequent boost, mice were bled through their tail veins and serum saved for analysis. collected serum was extensively absorbed on HIV Ab negative human antibody columns before being sterile filtered and reconcentrated back to their original volumes. Absorbed samples were stored as small samples at −70 C. until screened. Purification of Sera Serum antibodies were purified from hybridoma ascites fluid by sequential ammonium sulfate precipitation and protein A-sepharose (Sigma) chromatography. Beta was gradually made 50% ammonium sulfate by the addition of an equal volume of saturated ammonium sulfate at 4° C. with stirring. The solution was stirred for an additional 60 minutes to allow immunoglobulins to precipitate completely. The precipitate was collected by centrifugation at 15000x g for 15 min, and resuspended in phosphate-buffered saline (PBS; 188 mM NaCl, 10mM PO4, pH 7.2). The resulting immunoglobulin solution was dialyzed for 24 hr against PBS with at least three changes. The ammonium sulfate cut was then clarified by centrifugation and passed over a protein A-sepharose column. The column was washed with normal saline until the $OD_{280}$ of the filtrate was less than 0.1. The bound immunoglobulin was then eluted with 3.5 M $MgCl_2$. Relevant fractions were pooled and dialyzed extensively against normal saline and then PBS, and filtered through a 0.45 um filter. The antibody solution was concentrated using an Amicon concentrator under nitrogen pressure, and the protein concentration was determined using a Protein Assay Kit ( mioRad Labs, Richmond, Calif.)

Flow Cytometry

Cells were removed from tissue culture and washed twice in FACS medium (Hanks' balanced salt solution (Gibco) supplemented with 2% fetal calf serum, 0.2% sodium azide, and 10 mM Hepes). $1 \times 10^5$ to $1 \times 10^6$ cells were incubated on 0.1 ml of FACS medium with antibody or control supernatant in a volume of 0.1 ml for 1 hr at 4° C. Cells were diluted in 2.5 ml of FACS medium, pelleted by centrifugation at $1000 \times g$ and washed twice with 2.5 ml of FACS medium per wash. Following the final wash, the cell pellet was gently resuspended and cells incubated with 0.1 ml of FITC-conjugated rabbit anti-mouse 1 gG (reactive with antibody heavy and light chains, Miles Laboratories) diluted 1:20–1:50 in FACS medium for 1 hr at 4° C. Cells were diluted and washed as after the first incubation. The cell pellet was finally resuspended and the cells fixed in 0.5–1.0 ml 2% paraformaldehyde-PBS. Samples were run on an Becton Dickinson FACS IV. 20,000 cells per sample were routinely analyzed. Specific fluorescence was quantitated by subtracting the median fluorescence channel of cells stained with FITC-conjugated rabbit anti-mouse immunoglobulin alone (negative control) from the median fluorescence channel of cells stained with specific antibody followed by FITC-conjugated rabbit anti-mouse immunoglobulin (positive staining).

CD4+ cell lines, Molt 4 and Sup T1 both demonstrated strong specific reactivities with anti-H156. In addition, human cell lines including HSB (American Type Culture Collection number CCL120.1), a CD4-T cell line, was also reactive. This demonstrates that the determinant recognized by the anti-idiotypic sera is not CD4. To determine if the reactivity pattern of the antiidiotype antisera was similar to the reported species tropism of HIV, the binding of the anti-H156 sera to murine cells was examined. Negligible reactivity was observed (FIGS. 1-9). Absorption with murine L cells prior to staining both human and other murine cell lines removed all reactivity to murine cells without affecting the reactivity to human cells. When the experiment was performed with the pooled AIDS immunoglobulin generated anti-idiotypic antisera, no staining of human or murine cell lines was seen. The surface reactivity pattern of the anti-H156 antisera appears to be due to components of the human cell lines examined, and distinct from the HIV-1 receptor CD4. This structure correlates with the species tropism reported for HIV-1 in inducing productive syncytia formation.

Immunoprecipitation Protocol

Cell lines are precultured in methionine and cysteine free RPMI (Gibco)+10% dialyzed FCS and labeled for 16 hrs. with media supplemented with $^{35}$S-cysteine and $^{35}$S-methionine (100 uCi/ml) and lysates prepared and precleared as described in Sodroski et al., Nature 322: 470, (1986). Portions (200 ul) of cleared lysates are added to 20 ul of Protein A-Agarose beads preincubated with serum and rotated for 3 hours at 4° C. Beads are washed sequentially in lysing buffer (LB): LB containing 0.5 M NaCl; and LB with 0.1% sodium dodecyl sulfate (SDS). The adsorbed material is eluted by heating at 100° C. for 3 minutes in 50 ul of sample buffer [0.01M tris, pH 8.0, containing 2% SDS, 5% 2-mercaptoethanol (by volume), bromophenol blue 25 ug/ml, and 10% glycerol (by volume)], and analyzed on 7.5% SDS-PAGE. The gels are then fixed, dried and autoradiographed at −70° on KODAK XAR TM autoradiography.

For competitive immunoprecipitation of virus envelope glycoproteins the basic procedure was modified. H156 protein A purified IgG was coupled to CnBr sepharose 4B as per manufacturers instructions (Sigma). 40 ul of H156 beads (approximately 32 ugs of H156 based on 80% coupling efficiency) were preincubated at 37° C. for 30 minutes on a circular rotator with 50 ul of the following reagents (see FIG. 10): nothing (lane 1), H156 serum (lane 2), normal mouse sera (NMS) (lane 3), anti-pAIg mouse sera (lane 4), or anti-H156 mouse sera, for 30 minutes on a circulator rotator. The serum was then chilled on ice for 15 minutes and equal counts of $^{35}$S-met labeled precleared cell lysate was added to each Eppendorf test tube and precipitated as described in Sodrosfsky et al., Nature 322: 470, (1986), which is incorporated herein by reference.

Figure 10:
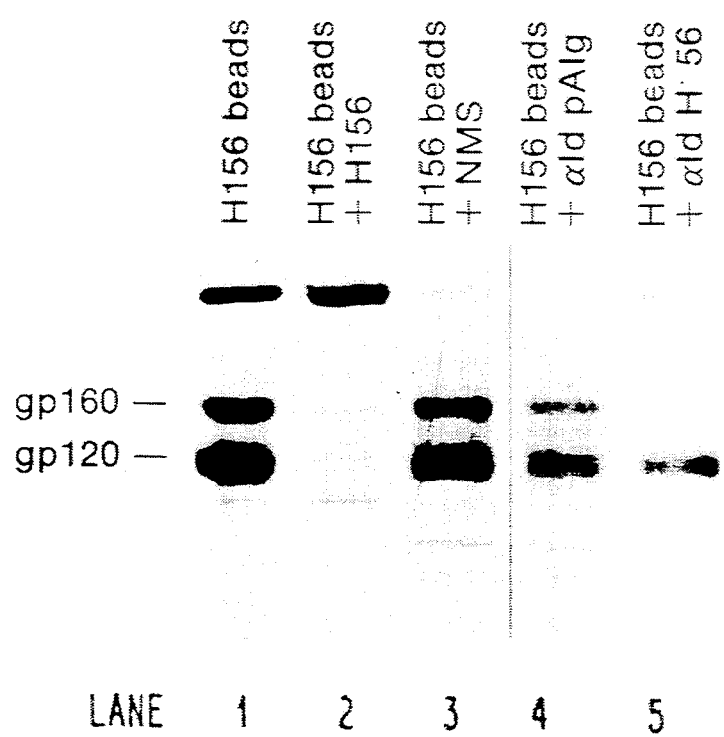
FIG. 10 shows competitive immunoprecipitation of virus envelope glycoproteins.

The anti-idiotypic antibodies blocked the ability of H156 antibody to precipitate gp160 but only minimally blocked gp120 immunoprecipitation. In contrast the pooled AIDS patient anti-idiotypic antisera did not exhibit complete blocking of either glycoprotein (FIG. 10). This result supports competitive immunoblotting data in that the predominant anti-idiotypic response is directed against antibodies specific for gp41. The studies also corroborate previously published observations such as those of McCune et al. Cell 53: 55, (1988) that the epitopes of the free gp120 and covalently linked gp120-gp41 (gp 160) are not identical.

While H156 sera blocks all reactivity with HIV-1 envelope glycoproteins gp160 and gp120, NMS exhibits no blocking ability, anti-pAIg exhibits the ability to partially block both gp160 and gp120 reactivities. Anti-H156 mouse sera partially blocks gp120 reactivity but specifically and repeatedly blocks all reactivity of H156 with gp160 envelope glycoprotein precursor protein.

Twelve out of twelve mice immunized with H156 produced this identical dominant immune response supporting our observation of a dominant idiotype in H156 sera directed at gp41. This result supports competitive immunoblotting data in that the predominant anti-idiotypic response is directed against antibodies specific for gp41.

Immunoblotting

Cell lines productively infected with HIV-1 are lysed in lysing buffer (0.02M tris and 0.12 M NaCl, pH 8.0, with 0.2 mM phenylethylsulfonyl fluoride, 0.2 mM EGTA, 0.2 mM NaF, 5 ug/ml of aprotinin, 0.2% sodium deoxycholate, and 0.5% by volume Nonidet P-40). Lysates are boiled for 5 minutes in 3% SDS, and approximately 15 ug of protein per lane is separated on 10% SDS-PAGE, electrotransferred to nitrocellulose and reacted with serum on control antisera. For competitive Western analysis the electrotransferred filters were reacted with pooled AIDS patient immunoglobulin on control sera at a concentration of 1 mg/ml after a 30 minute pre-incubation 50 ngs of $I^{125}$ labeled H156 purified IgG or IgM was added and allowed to incubate a further 1 hr. with agitation at 25° C. After extensive washing the blot was exposed to KODAK XAR TM autoradiography film at −70° C. for 24 hrs. Relevant bands were subjected to densitometry tracing for quantitation of specific reactivity with virus envelope glycoprotein gp41 or gp120.

Most reactivity to gp120 was inhibited by pretreatment of the nitrocellulose with pooled AIDS immunoglobulin. In contrast, significant reactivity for envelope glycoprotein gp41 remained after binding pooled AIDS immunoglobulin to it. This reflects H156 reactivity with unique epitopes expressed on gp41. These reactivities are not present in significant amounts in the pooled AIDS sera.

A 95% reduction in the reactivity to gp120 was produced by pretreatment of the nitrocellulose with pooled AIDS patient immunoglobulin (pAIg). In contrast, 90% of the reactivity for envelope glycoprotein gp41 remained after blocking with pAIg. This reflects H156 reactivity with unique epitopes expressed on gp41.

Radioimmunoassay

Figure 11:
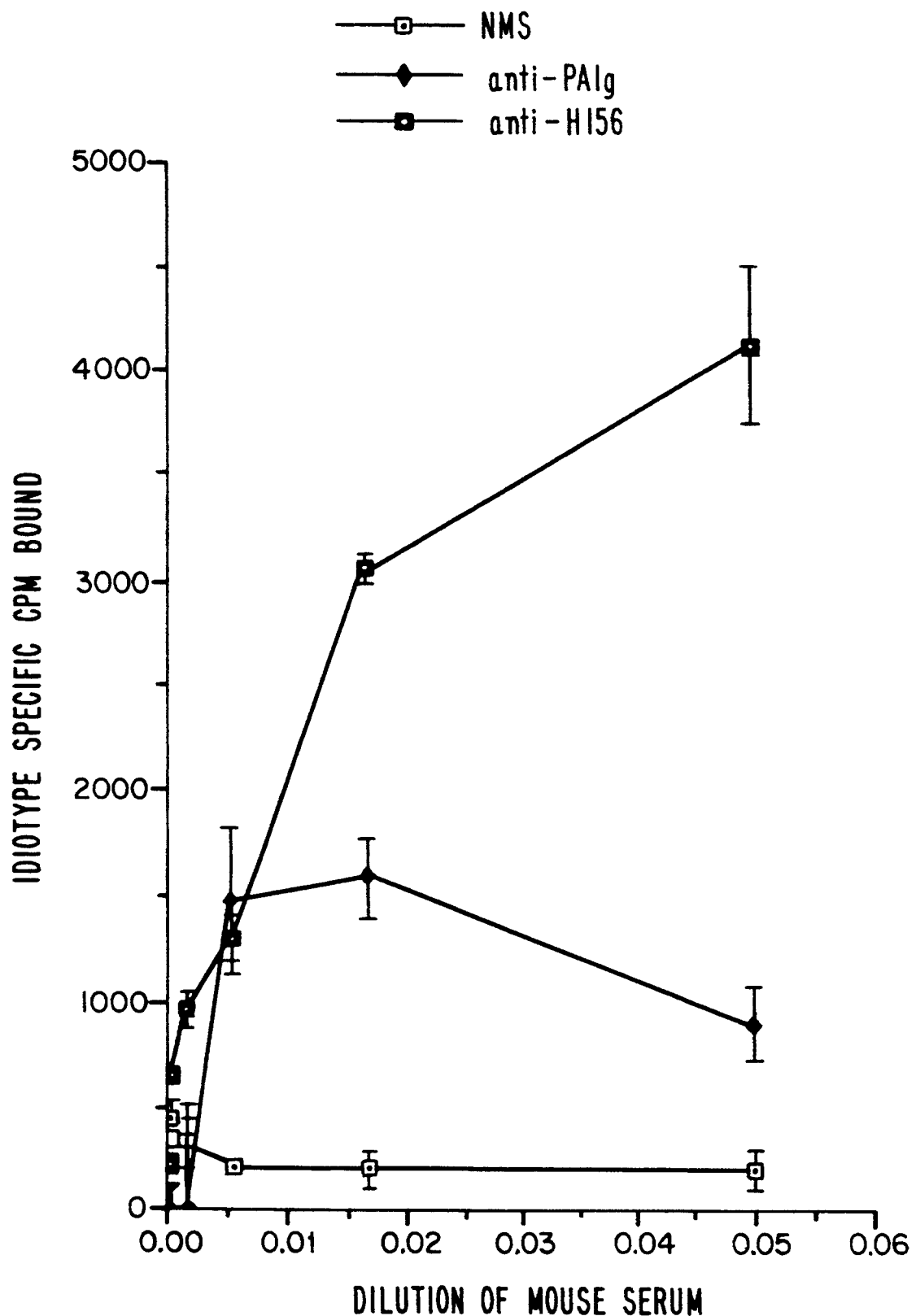
FIG. 11 shows idiotypic specific binding to H156.

Radioimmunoassay (RIA) analysis of the anti-idiotypic antibody following the procedure of Burstin et al., Virology 117: 146, (1982). RIA analysis demonstrated specific responses against the immunizing immunoglobulins with minimal binding to normal human immunoglobulin (FIG. 11). Mouse anti-H156 was compared with mouse anti-pAIg (pooled AIDS patient immunoglobulin) and normal mouse serum (NMS) for idiotype specific binding to H156. Both the anti-H156 and anti-pAIg showed specific binding to pAIg consistent with the presence of public idiotypes in both pAIGg and H156 relevant to HIV-1 exposure. However, anti-H156 demonstrated much greater idiotypic specific binding activity to H156 than anti-pAIg, while NMS showed negligible binding to either immunoglobulin. These data demonstrate the anti-idiotypic nature of anti-H156 as well as the presence of private idiotypes present in the H156 sera not represented in the pAIg sera.

Characterization of Host Cell Receptor (Second Receptor)

Cell lines (human HSB (American Type culture Collection number CCL120.1), ST, Sup T1 and HeLa (American Type Culture Collection number CCL2) and murine L cells and NIH 3T3 cells) are precultured in methionine and cysteine free RPMI (Gibco)+10% dialyzed FCS and labeled for 16 hrs. with media supplemented with $^{35}$S-cysteine and $^{35}$S-methionine (100 uCi/ml) and lysates prepared and precleared as described in Sodroski et al., Nature 322: 470, (1986). Portions (200 ul) of cleared lysates are added to 20 ul of Protein A-Agarose beads preincubated with serum and rotated for 3 hours at 4° C. Beads are washed sequentially in lysing buffer (LB); LB containing 0.5 M NaCl; and LB with 0.1% sodium dodecyl sulfate (SDS). The adsorbed material is eluted by heating at 100° C. for 3 minutes in 50 ul of sample buffer [0.01 M tris, pH 8.0, containing 2% SDS, 5% 2-mercaptoethanol (by volume), bromophenol blue 25 ug/ml, and 10% glycerol (by volume)], and analyzed on 7.5% SDS-PAGE. The gels are then fixed, dried and autoradiographed at −70° on KODAK XAR TM autoradiography.

Figure 12:
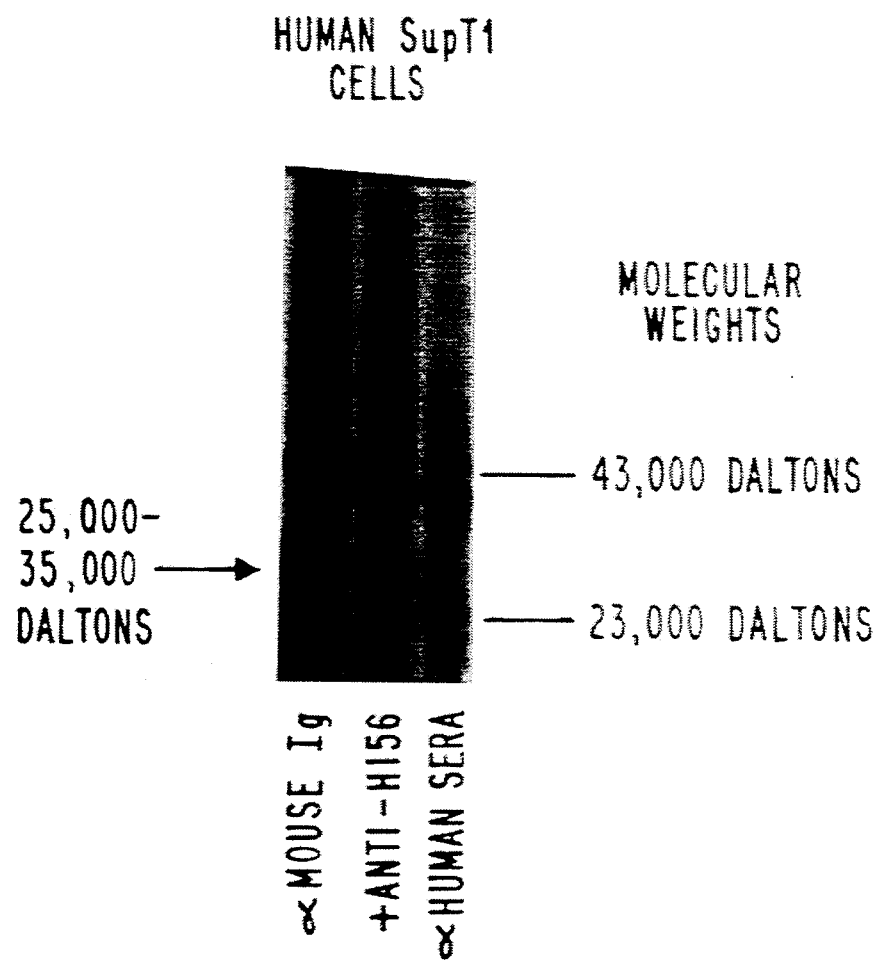
FIGS. 12 and 13 show gel electrophoresis of second receptor glycoproteins.
Figure 13:
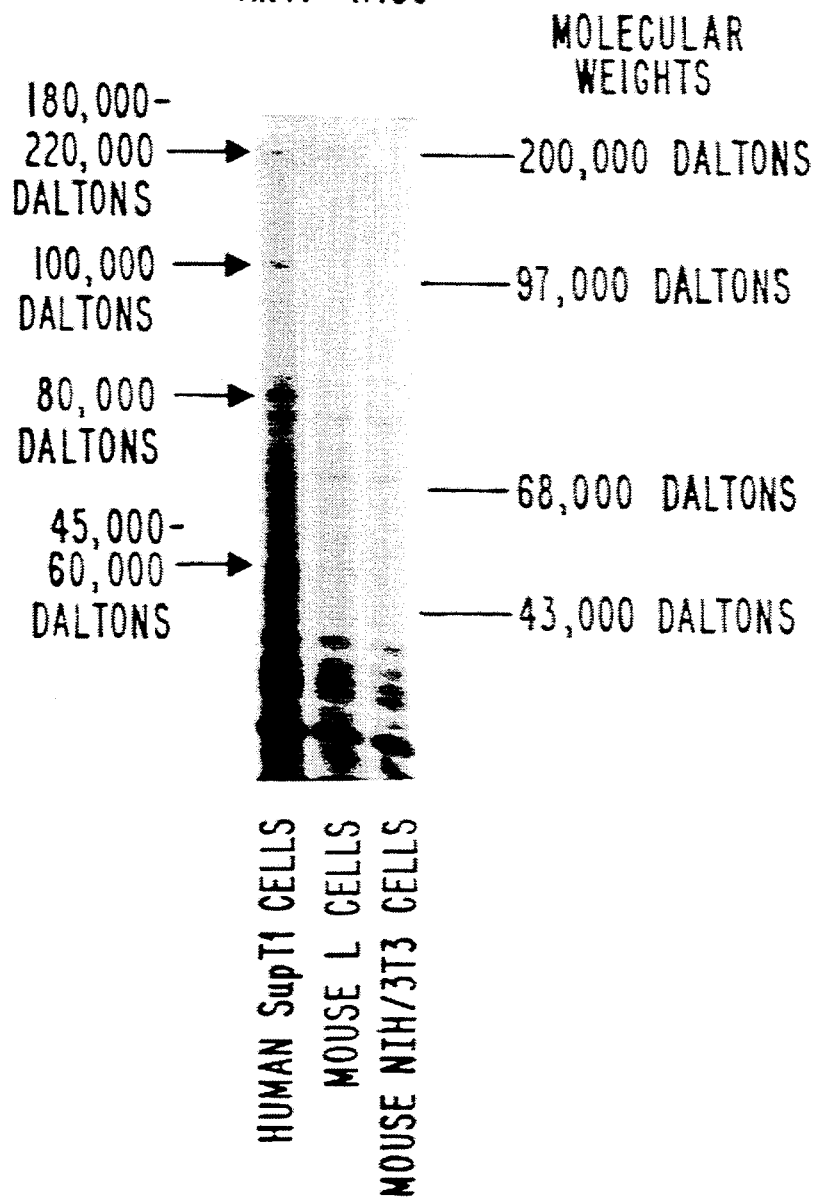

As shown in FIGS. 12 and 13, anti-H156 specifically immunoprecipitates, from human cells and not from murine cells, several polypeptides including a major band at 25-35Kd, as well as minor bands at 45-60 Kd, 80-100Kd and 180-220 Kd.

Protective Peptides

PEPTIDES: Peptides were synthesized by the Protein Chemistry Laboratory of the University of Pennsylvania using conventional techniques. Amino terminal cysteine residues were added to the sequence of some peptides during synthesis for coupling to proteins. Peptides were purified, and conjugated to keyhole limpet hemocyanin (KLH) by the following method. To 15 mg of keyhole limpet hemocyanin (KLH, Sigma) in 1 ml of 50 sodium bicarbonate was added 5 mg of sulfo-MBS (Pierce). After thirty minutes at room temperature, the KLH was separated from excess sulfo-MBS by gel filtration on Sephadex G50. Fifty mg of the peptide in 1 ml of sodium bicarbonate was added to the KLH and allowed to react for a further 3 hours. The macromolecular conjugate was separated from unconjugated peptide by gel filtration on Sephadex G50. The peptide-KLH conjugate was suspended in phosphate-buffered saline (20 mM sodium phosphate, 154 mM NaCl, pH 7.2) at a concentration of 1 mg/ml.

PATIENTS: H156 represents serum from an HIV-1 infected individual who was asymptotic, and which demonstrated a uniquely high degree of syncytia inhibitory activity by several isolates of HIV-1, Weiner et al. (1989) "Non-CDA molecules on human cells important in HIV-1 cell entry."Vaccines 89, Cold Spring Harbor Laboratories, CSH, N.Y. pp. 115–120.

EPITOPE DETERMINATION: H156 was utilized to obtain purified IgG and directly radioiodinated as in Williams et al, Proc. Natl. Acad. Sci. USA 85:6488 (1988). Radioimmunoassay plates were coated with various peptides derived from the HIV-1 gp160 sequence, including the peptides shown in Table 1, and binding of purified radioiodinated M156 IgG to these peptides was carried out as described in Williams supra.

Several peptides were chosen for further study on the basis of the ability of H156 to bind these peptides at a much higher level than IgG from control AIDS patients IgG prepared in the same manner. These are detailed in Table 2. Two of these peptides were designated F160 (bearing the sequence of residues 150–170 of gp160), and F560 (bearing the sequence of residues 550–570 of gp160) (see Table 1).

IMMUNIZATION: NZW rabbits were injected subcutaneously with 50–100 µg of peptide-KLH conjugate or unconjugated peptide emulsified with 50–100 µl of Freund's complete adjuvant. After two weeks, the rabbits received a similar injection using incomplete adjuvant. Further booster injections were performed subcutaneously at two-week intervals using 50 µg of the conjugate without adjuvant. Serum was obtained from immune animals following the third boost, and utilized without heat inactivation.

Serum was obtained one week after the fifth injection and assayed for anti-peptide antibodies using a solid-phase radioimmunoassay. For this assay, 2.5 µug of peptide in 50 of water was dried onto each well of a 96-well polyvinyl chloride microtiter place. A solution of bovine serum albumin (20 mg/ml) in phosphate-buffered saline containing 0.1% sodium azide was added to fill each well. These plates were stored at 4° C. until use. Preimmune and immune sera from each mouse were diluted into albumin-containing buffer and added to the drained wells. The plates were incubated overnight at room temperature, and the wells were then washed with phosphate-buffered saline. [125I]-goat anti-mouse light chains (40,000 cpm/well, Southern Biotechnology Associates, iodinated using a modification of the chloramine T method as described in Hunter and Greenwood, (1962) Nature 194: 495–496 in 100 µl of phosphate-buffered saline containing bovine serum albumin was added to each well and incubated for two hours at 37° C. The plate was then washed several times with water and the radioactivity in each well determined with an automated gamma counter.

CYTOFLUORIMETRY: The ability of immune rabbit sera to stain gp120 and gp160 bearing cells was determined by cytofluorimetry as described in Williams et al., Proc. Natl. Acad. Sci. USA 85:6488 (1988). Rabbit sera were used as dilutions of 1:10 to 1:100. Positive staining was determined by % positive of >10 or Δ mean channel florescence of >8.

CELLS LYSIS: Cells were lysed by antibody and complement treatment as described in Williams et al., (1987) "The cellular basis for the 1a restriction in murine experimental autoimmune thyroiditis", Cell. Immunol. 110:35–45. Rabbit antisera was utilized at dilutions of 1:2–1:128. Those considered positive lysed cells at dilutions of at least 1:16. Lysis of cells was determined by direct visualization and cell counting. Lysis was considered present if >90% of the cells originally present in the sample were deleted.

Staining and Lysis of Cells by Immune Rabbit Sera

To construct cells that bore gp120 without gp41, culture supernatants from CHO/gp160 cells, which shed gp120, were incubated with H9 cells, which bear large amounts of CD4. The cells were washed, and utilized in the cell lysis and cytofluorimetry assays described herein.

CELLS: Chinese hamster ovary (CHO) cells, and CHO cells that are infected with and express HIV-1 gp160 (CHO/gp160) have been described in Weiner et al., 1989. Non-CD4 molecules on human cells important in HIV-1 cell entry. Vaccines 89. Cold Spring Harbor Laboratories, CSH, N.Y., 115–120. H9 is a human T cell line that expresses large amounts of CD4 molecules. All cells were grown in RPMI 1640 with added penicillin/streptomycin, L-glutamine, and 10% fetal calf serum (culture media).

PREPARATION OF gp120 CONTAINING SUPERNATANT: CHO/gp160 cells were selected for secretion of large amounts of gp120. These cells were grown in culture media to a high cell density, supernatants harvested, centrifuged, and filtered through a 0.45 um filter prior to use.

By comparing results utilizing CHO cells, H9 cells, H9 cells incubated with supernatant from CHO/gp160, CHO/gp160 cells and H9 cells infected with HTLV-111b (Weiner et al. (1989) "Non-CD4 molecules on human cells important in HIV-1 cell entry" Vaccines 89, Cold Spring Harbor Laboratories, CSH, N.Y. pp. 115–120, binding and lysis via gp120 and gp41 were distinguished. The results are shown in Table 2.

TABLE 2

STAINING AND LYSIS OF CELL LINES BY IMMUNE RABBIT SERA

| Cell Line | Antibody To: | Complement Mediated Lysis | Flow Cytometry Staining |
|---|---|---|---|
| CHO | F560-KLH | − | − |
| CHO | F160 | − | − |
| H9 | F560-KLH | − | − |
| H9 | F160 | − | − |
| H9 + GP120[a] | F560-LH | − | − |
| H9 + GP120 | F160 | + | + |
| CHO/gp160 | F560-KLH | + | + |
| CHO/gp160 | F160 | + | + |
| H9/111[b] | F560-KLH | + | + |
| H9/111b | F160 | + | + |

[a]H9 cell preincubated with culture supernatant from CHO/gp160 cells containing gp120
[b]H9 cells infected with the HTLV-111b isolate of HIV-1.

As shown in Table 2, antibodies to peptide F560 coupled to KLH do not lyse H9 cells that have been proincubated with culture supernatant from CHO/gp160 cells containing gp120 whereas antibodies to peptide F160 did bind to these cells. This result indicates that these anti-F560-KLH antibodies are specific for a region of 9160 that becomes gp41 and that the peptide F560 defines an epitope of gp41. Anti-F160 antibodies are specific for a region of gp160 that becomes gp120 and the peptide thus defines an epitope of gp120.

Significance

An important structural component of HIV virions is the membrane spanning molecule gp41. During vital replication, the HIV envelope protein is synthesized as a large unit, termed gp160, which is subsequently cleaved into gp120 and gp41. Gp120 forms the outer membrane glycoprotein of HIV, while gp41 remains anchored in the membrane acting as an anchor to which gp120 attaches. While gp120 is capable of being shed into the media, gp41 remains anchored in the membrane of the virion or of the infected cell. It is important to note that the sequence of the F560 defined epitope is completely covered in all HIV-1 isolates examined to date. It is expected that analogous regions will be present in other retroviruses.

Serum with potent syncytia inhibitory activity was obtained from a healthy HIV-1 infected individual. It was hypothesized that this individual's antibody response would recognize regions of the HIV envelope important in the development of protective immunity. By comparing this individual's antibody profile for binding to gp160 derived peptides to the profile of antibodies from symptomatic HIV-1 infected individuals, Applicants were able to detect unique reactivities to several peptide regions. This included amino acids 150–170 of gp160 (contained on gp120), and amino acids 550–570 of gp160 (contained on gp41). Applicants then immunized rabbits with these peptides (either uncoupled or coupled to KLH), and tested their antisera for binding to gp120/gp41, and for their ability to lyse cells bearing gp120 and/or gp41. Antibodies specific for the peptides bound to gp120/gp41 and were able to lyse cells bearing gp120 and/or gp41. The peptide corresponding to a mind acids 550–570 of gp160 (F560) which is contained on gp41 is especially useful because it defines an epitope on gp41, the integral membrane protein of HIV-1. gp41 is not shed by the virus or infected cells but remains anchored in the membrane. Antibodies specific for the peptide F560 bind to gp41 on infected cells, initiating complement mediated lysis of the infectd cell. Antibodies specific for the peptide F560 do not bind to uninfected cells that express CD4 receptors that have gp120 bound thereon thus sparing the "innocent bystander" cells from lysis.

What is claimed is:

1. A peptide consisting of the amino acid sequence gly-glu-ile-lys-asn-cys-ser-phe-asn-ile-ser-thr-ser-ile-arg-gly-lys-val-gln-lys-glu-tyr-ala.

2. A peptide consisting of the amino acid sequence asn-gly-asn-ala-glu-glu-val-val-ile-arg-ser-ala-asn-phe-thr-asp-asn-ala-lys-thr-ile-ile-val.

3. A peptide consisting of the amino acid sequence cys-asn-ile-ser-arg-ala-lys-trp-asn-asn-thr-leu-lys-gln-ile-asp-ser-lys-leu-arg-glu-gln-phe.

4. A peptide consisting of the amino acid sequence gly-ser-asp-thr-ile-thr-leu-pro-cys-arg-ile-lys-gln-ile-ile-asn-met-trp-gln-glu-val-gly-lys.

5. A peptide consisting of the amino acid sequence val-gln-gln-gln-asn-asn-leu-leu-arg-ala-thr-glu-ala-gln-his-leu-leu-gln-leu-thr-val-trp-gly-ile-lys-gln-leu-gln.

* * * * *